(12) United States Patent
Widdison et al.

(10) Patent No.: US 7,301,019 B2
(45) Date of Patent: Nov. 27, 2007

(54) METHOD FOR THE PREPARATION OF MAYTANSINOID ESTERS

(75) Inventors: Wayne C. Widdison, Somerville, MA (US); Ravi V. J. Chari, Newton, MA (US)

(73) Assignee: Immunogen, Inc., Cambridge, MA (US)

( * ) Notice: Subject to any disclaimer, the term of this patent is extended or adjusted under 35 U.S.C. 154(b) by 109 days.

(21) Appl. No.: 11/334,478

(22) Filed: Jan. 19, 2006

(65) Prior Publication Data

US 2006/0167245 A1  Jul. 27, 2006

Related U.S. Application Data

(60) Provisional application No. 60/644,984, filed on Jan. 21, 2005.

(51) Int. Cl.
*C07D 491/12* (2006.01)
*C07D 498/06* (2006.01)

(52) U.S. Cl. .................................................. 540/456
(58) Field of Classification Search ................ 540/456
See application file for complete search history.

(56) References Cited

U.S. PATENT DOCUMENTS 6,333,410 B1  12/2001  Chari et al.

OTHER PUBLICATIONS

A. Kawai, et al., Chemical Modification of Ansamitocins. III Synthesis and Biological Effects of 3- Acyl Esters of Maytansinol, Chem. Pharm. Bull, 1984, pp. 3441-3451, vol. 32.

*Primary Examiner*—Bruck Kifle
(74) *Attorney, Agent, or Firm*—Sughrue Mion Pllc.

(57) ABSTRACT

Improved processes for the preparation and purification of maytansinoid esters, especially thiol and disulfide-containing maytansinoids are described. In one aspect the process comprises a process of making a maytansinoid ester comprising forming an anion of maytansinol or a maytansinoid bearing a free C-3 hydroxyl moiety and reacting the anion with an activated carboxyl compound to thereby produce the maytansinoid ester.

27 Claims, No Drawings

METHOD FOR THE PREPARATION OF MAYTANSINOID ESTERS

This application claims priority to U.S. provisional application Ser. No. 60/644,984, filed Jan. 21, 2005, the entire disclosure of which is expressly incorporated herein by reference.

FIELD OF THE INVENTION

The present invention relates to a method for preparing maytansinoids that are substantially single diastereomers. More specifically, the invention relates to a method for preparing thiol or disulfide-containing maytansinoid esters, which substantially exist as a single diastereomer with the L-stereochemistry in the side chain at the C-3 position. These maytansinoid esters are cytotoxic agents that can be used as therapeutic agents by linking them to a cell binding agent, through the thiol group, and then delivering them to a specific cell population in a targeted fashion.

BACKGROUND OF THE INVENTION

Maytansinoids are highly cytotoxic drugs. Maytansine was first isolated by Kupchan et al. from the east African shrub *Maytenus serrata* and shown to be 100 to 1000 fold more cytotoxic than conventional cancer chemotherapeutic agents like methotrexate, daunorubicin, and vincristine (U.S. Pat. No. 3,896,111). Subsequently it was discovered that some microbes also produce maytansinoids, such as maytansinol and C-3 esters of maytansinol (U.S. Pat. No. 4,151,042). Synthetic C-3 esters of maytansinol and analogues of maytansinol have also been reported (Kupchan et al., 21 J. Med. Chem. 31-37 (1978); Higashide et al., 270 Nature 721-722 (1977); Kawai et al., 32 Chem. Pharm. Bull. 3441-3451 (1984)). Examples of analogues of maytansinol from which C-3 esters have been prepared include maytansinol with modifications on the aromatic ring (e.g. dechloro) or at the C-9, C-14 (e.g. hydroxylated methyl group), C-15, C-18, C-20 and C-4,5.

The naturally occurring and synthetic C-3 esters can be classified into two groups:

(a) C-3 esters with simple carboxylic acids (U.S. Pat. Nos. 4,248,870; 4,265,814; 4,308,268; 4,308,269; 4,309,428; 4,317,821; 4,322,348; and 4,331,598), and (b) C-3 esters with derivatives of N-methyl-L-alanine (U.S. Pat. Nos. 4,137,230; 4,260,608; 5,208,020; 5,416,064; and 12 Chem. Pharm. Bull. 3441 (1984)).

Esters of group (b) were found to be much more cytotoxic than esters of group (a). Because maytansinoids are highly cytotoxic, they were expected to be of use in the treatment of many diseases, such as cancer. This expectation has yet to be realized. Clinical trials with maytansine were not favorable due to a number of side effects (Issel et al., 5 Can. Trtmnt. Rev. 199-207 (1978)). Adverse effects to the central nervous system and gastrointestinal symptoms were responsible for some patients refusing further therapy (Issel at 204), and it appeared that maytansine was associated with peripheral neuropathy that might be cumulative (Issel at 207).

However, forms of maytansinoids that are highly cytotoxic, yet can still effectively be used in the treatment of many diseases, have been described (U.S. Pat. Nos. 5,208,020 and 5,416,064; Chari et al., 52 Cancer Res. 127-131 (1992); Liu et al., 93 Proc. Natl. Acad. Sci. 8618-8623 (1996)).

U.S. Pat. Nos. 5,208,020, 5,416,064 and 6,333,410 disclose that a thiol-containing maytansinoid may be produced by first converting a maytansinoid bearing an ester group into maytansinol, then esterifying the resulting maytansinol with a disulfide-containing acyl N-methyl-L-alanine to yield disulfide-containing maytansinoids. Reduction of the disulfide group with dithiothreitol gave the thiol-containing maytansinoids. However, this process involves several inefficient steps that are cumbersome and result in only moderate yields.

More specifically, maytansinol is first derived from maytansine or other esters of maytansinol by reductive cleavage, such as with lithium aluminum hydride. (Kupchan, S. M. et al., 21 J. Med. Chem. 31-37 (1978); U.S. Pat. No. 4,360,462). It is also possible to isolate maytansinol from the microorganism *Nocardia* (see Higashide et al., U.S. Pat. No. 4,151,042). In one specific example, the conversion of Ansamitocin P-3 into maytansinol by reductive hydrolysis with lithium aluminum hydride in tetrahydrofuran at −5° C. is described (U.S. Pat. No. 4,162,940).

The next step in the process is the conversion of maytansinol to different ester derivatives using N-methyl-L-alanine derivatives, and suitable agents such as dicyclohexylcarbodiimide (DCC) and catalytic amounts of zinc chloride (see U.S. Pat. Nos. 4,137,230, 4,260,609, 5,208,020, 5,416,064 and 6,333,410; Kawai et al., 32 Chem. Pharm. Bull. 3441-3951 (1984)). In all cases, two diastereomeric products containing the D and L-aminoacyl side chains result, as does a small portion of unreacted maytansinol. In the processes previously described (Kupchan, S. M., 21 J. Med. Chem. 31-37 (1978); U.S. Pat. No. 4,360,462; U.S. Pat. No. 6,333,410), the desired L-aminoacyl ester is obtained after purification over two silica gel columns or a combination of silica gel columns and HPLC columns. In addition, because of complete racemization, the isolated yield of the desired L-aminoacyl isomer is only around 30%. Hence, the processes described thus far are cumbersome, uneconomical and poorly amenable to use on an industrial scale.

Accordingly, an improved process for the preparation and purification of thiol-containing maytansinoids, which predominantly results in the synthesis of the desired diastereomers, is greatly needed.

SUMMARY OF THE INVENTION

The present invention encompasses a process of making a maytansinoid ester comprising forming an anion of maytansinol or other maytansinoids bearing a free C-3 hydroxyl moiety and reacting the anion with an activated carboxyl compound to thereby produce the maytansinoid ester.

The anion of maytansinol can be produced by reaction of maytansinol with a base.

The activated carboxyl compound, used to produce a maytansinoid ester, can be defined generally by the formula RCOX, wherein X is —OCOR' to give an anhydride or a mixed anhydride, or wherein X is a halide, an alkoxy group, an aryloxy group, or an imidazole and R and R' are the same or different and are selected from a linear, branched or cyclic alkyl or alkenyl having from 1 to 10 carbon atoms, or a substituted amino acid moiety, such as an N-methyl-L-alanyl moiety.

Such an activated carboxyl compound generally encompasses, but is not limited to, acid anhydrides, mixed anhydrides, cyclic anhydrides, acid halides, imidazolides, esters or a mixture thereof.

DETAILED DESCRIPTION OF THE INVENTION

The present invention provides an improved process for the preparation and purification of maytansinoid esters, especially thiol and disulfide-containing maytansinoid esters, which are substantially one diastereomer.

The term "substantially" as used herein refers to a desired maytansinoid diastereomer to be about or greater than around 75%, preferably, 75-80%, more preferably, 80-85%, and even more preferably, 85-100% diasteromerically pure.

In one aspect, the process of the present invention comprises forming an anion of maytansinol or other maytansinoids bearing a free C-3 hydroxyl moiety and reacting the anion with an activated carboxyl compound to thereby produce the maytansinoid ester.

The starting material for the method is maytansinol or any naturally occurring or synthetic maytansinoid bearing a free C-3 hydroxyl moiety.

Specific examples of suitable maytansinoids include, but are not limited to:

(1) C-19-dechloro (U.S. Pat. No. 4,256,746) (prepared by LAH reduction of ansamitocin P2); and (2) C-20-demethoxy, C-20-acyloxy (—OCOR), +/−dechloro (U.S. Pat. No. 4,294,757) (prepared by acylation using acyl chlorides).

Specific examples of suitable maytansinoids also include analogues of maytansinol having modifications of other positions such as:

(1) C-14-alkoxymethyl (demethoxy/$CH_2OR$) (U.S. Pat. No. 4,331,598);

(2) C-14-hydroxymethyl or acyloxymethyl ($CH_2OH$ or $CH_2OAc$) (U.S. Pat. No. 4,450,254) (prepared from *Nocardia*);

(3) C-15-hydroxy/acyloxy (U.S. Pat. No. 4,364,866) (prepared by the conversion of maytansinol by *Streptomyces*);

(4) C-15-methoxy (U.S. Pat. Nos. 4,313,946 and 4,315,929) (isolated from *Trewia nudiflora*);

(5) C-18-N-demethyl (U.S. Pat. Nos. 4,362,663 and 4,322,348) (prepared by the demethylation of maytansinol by *Streptomyces*); and (6) C-9-Alkoxy (Akimoto et. al. *Chem. Pharm. Bull.* (1984) vol 32, pg 2565).

The anion can be formed by any suitable reaction. For example, the maytansinol or other maytansinoids bearing a free C-3 hydroxyl moiety can be reacted with a non-aqueous base, such as a metal hexamethyldisilazide, selected from, but not limited to, zinc hexamethyldisilazide, sodium hexamethyldisilazide, lithium hexamethyldisilazide, and potassium hexamethyldisilazide; an alkyl metal or an aryl metal, selected from, but not limited to, methyl lithium, n-butyl lithium, tert-butyl lithium, phenyl lithium, lithium di-isopropylamide (LDA), pentyl sodium, and 2-phenyl isopropyl-potassium; a metal hydride, selected from, but not limited to, sodium hydride and potassium hydride; sodamide; and potassium amide.

Preferably, the non-aqueous base is zinc hexamethyldisilazide.

Those of ordinary skill in the art will readily recognize suitable activated carboxyl compounds useful for forming the ester by reaction with the anion. Examples of suitable activated carboxyl compounds include acid anhydrides such as carboxylic acid anhydrides, selected from, but not limited to, acetic anhydride and isobutyric anhydride and anhydrides of amino acid derivatives such as derivatives of N-methyl-L-alanine such as anhydrides of N-methyl-N-(3-methyldithio-1-oxopropyl)-L-alanine and N-methyl-N-(4-methyldithio-4-methyl-1-oxopentyl)-L-alanine; mixed anhydrides, selected from, but not limited to, mixed anhydrides between a phosphate or sulfate with the carboxylic acid moiety of alkanoic acids, such as, acetic acid, propionic acid, butyric acid, or an amino acid derivative such as the carboxylic acid moiety of N-methyl-alanine derivatives such as, but not limited to, N-methyl-N-(3-methyldithio-1-oxopropyl)-L-alanine and N-methyl-N-(4-methyldithio-4-methyl-1-oxopentyl)-L-alanine; cyclic anhydrides, selected from, but not limited to, an N-carboxyanhydride of N-methyl-L-alanine and an N-carboxyanhydride of N-methyl-D-alanine; acid halides selected from, but not limited to, acid fluorides, acid chlorides, acid bromides and acid iodides; acylimidazolides, selected from, but not limited to, acetyl chloride, acetyl fluoride, acid fluorides of amino acid derivatives such as the acid fluoride of N-methyl-N-(3-methyldithio-1-oxopropyl)-L-alanine or of N-methyl-N-(4-methyldithio-4-methyl-1-oxopentyl)-L-alanine; acyl substituted imidazolides, for example, the imidazolide of alkanoic acids, such as, acetic acid or propionic acid or an imidazolide of amino acid derivatives, for example, N-methyl-alanine derivatives such as N-methyl-N-(3-methyldithio-1-oxopropyl)-L-alanine and N-methyl-N-(4-methyldithio-4-methyl-1-oxopentyl)-L-alanine; and carboxyl esters selected from, but not limited to, N-hydroxysuccinimide esters, N-hydroxyphthalimide esters, para-nitrophenyl esters, ortho-nitrophenyl esters, dinitrophenyl esters, and pentafluorophenyl esters.

In another aspect of the invention, the activated carboxyl compound is represented by the formula RCOX, wherein X is —OCOR' to give an anhydride or a mixed anhydride, or wherein X is a halide, an alkoxy group, an aryloxy group, an imidazole or —OY, wherein Y is succinimide, phthalimide, aryl or substituted aryl, and R and R' are same or different and are selected from a linear, branched or cyclic alkyl or alkenyl having from 1 to 10 carbon atoms, or a substituted amino acid moiety, such as an N-methyl-L-alanyl moiety.

Preferably, X is fluoride, chloride, bromide, iodide, pyridyl, imidazolyl, substituted imidazolyl, or —OY, wherein Y is succinimide, phthalimide, aryl or substituted aryl, such as para-nitrophenyl, ortho-nitrophenyl, dinitrophenyl, and pentaflurophenyl.

In a further aspect of the invention, the activated carboxyl compound is represented by a carboxyl-activated amino acid containing compound of the formula (Ia), (Ib), (Ic) or (Id):

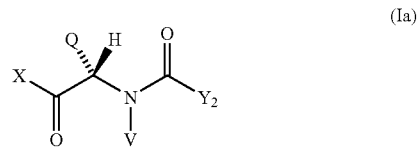

(Ia)

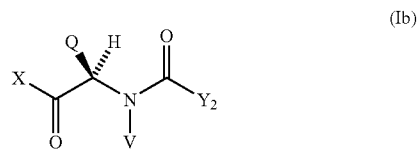

(Ib)

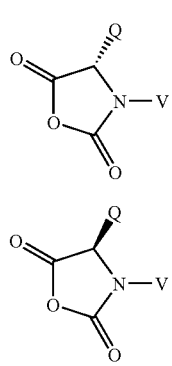

X represents a halide, an alkoxy group, an aryloxy group, an imidazole, or —OY, wherein Y represents succinimide, phthalimide, aryl or substituted aryl or X is chosen such that it forms an anhydride or mixed anhydride; Q represents H or a branched or linear alkyl group; and V represents H, or a branched or linear alkyl group; and $Y_2$ represents $(CR_7R_8)_l$ $(CR_5R_6)_m(CR_3R_4)_nCR_1R_2(SZ_2)_p$, wherein:

$R_1$ and $R_2$ are each independently H, linear, branched or cyclic alkyl or alkenyl having from 1 to 10 carbon atoms, such as $CH_3$ and $C_2H_5$, phenyl or substituted phenyl, and in addition $R_2$ can be H;

$R_3$, $R_4$, $R_5$, $R_6$, $R_7$ and $R_8$ are each independently H, linear, branched or cyclic alkyl or alkenyl having from 1 to 10 carbon atoms, such as $CH_3$ and $C_2H_5$, phenyl or substitued phenyl;

l, m and n are each independently 0 or an integer of from 1 to 5;

$Z_2$ is $R_9$, $SR_9$ or $COR_9$, wherein $R_9$ is linear alkyl, branched alkyl or cyclic alkyl having from 1 to 10 carbon atoms, or simple or substituted aryl or heterocyclic; and p is either 0 or 1.

In addition, X can be —$OCOR_9$, wherein $R_9$ is as defined above, or X gives a symmetrical anhydride of formula (Ia) or (Ib).

Suitable alkyl groups represented by Q and V include, but are not limited to, $C_1$-$C_{10}$ alkyl groups, such as methyl, ethyl, propyl, isopropyl, butyl, isobutyl, tert-butyl, cyclo pentyl and the like.

Preferably X represents fluoride, chloride, bromide, iodide, pyridyl, imidazolyl, substituted imidazolyl, such as but limited to alkyl imidazolyl in which the alkyl group is either linear branched or cyclic such as methyl imidazolyl, ethyl imidazolyl, cyclopentyl imidazolyl, or —OY, wherein Y represents succinimide, phthalimide, aryl or substituted aryl.

Aryl means aryl containing 6 to 15 carbon atoms and includes, but is not limited to, phenyl, biphenyl, 1-naphthyl and 2-naphthyl.

Examples of substituted phenyl and substituted aryl include para-nitrophenyl, ortho-nitrophenyl, dinitrophenyl, and pentafluorophenyl.

Examples of heterocyclic include pyridyl and substituted pyridyl, furyl, oxazolyl, thienyl, thiazolyl, indolyl, morpholino, piperidino and piperazino.

Preferably, the activated carboxyl compound is an acid fluoride or an acid anhydride.

Reaction conditions are readily determined by one of ordinary skill in the art.

The time required for the reaction can be easily monitored by one skilled in the art using techniques such as but not limited to high pressure chromatography or thin layer chromatography. A typical reaction is completed after stirring over night but may be performed at a slower or a faster rate depending on various factors, such as, temperature and concentration of the substituents. The reaction can be performed between –20° C. through 80° C., preferably between –10° C. and 60° C., more preferably between –10° C. to 40° C., and most preferably between 0° C. and 35° C.

Suitable solvents are readily determined by one of ordinary skill in the art, and include, but are not limited to, tetrahydrofuran or substituted tetrahydrofuran, hexanes, ethers such as diethyl ether, dimethoxyethane, dioxane, or a mixture thereof.

Quenching conditions include, but are not limited to quenching with water, alcohols, such as methanol, ethanol, n-propanol or isopropanol; acids such as hydrochloric acid, formic acid, acetic acid and phosphoric acid, or with bases such as sodium or potassium carbonate, sodium or potassium bicarbonate, sodium or potassium hydroxide.

Purification conditions are readily determined by one of ordinary skill in the art, and include, but are not limited to, column chromatography on silica gel or alumina, preparatory thin layer chromatography, HPLC, counter current distribution and recrystallization.

The invention will now be described by reference to specific examples. However, the invention is not limited thereto. Unless otherwise specified, all percents, ratios, etc. are by weight.

EXAMPLES

Reaction Scheme.

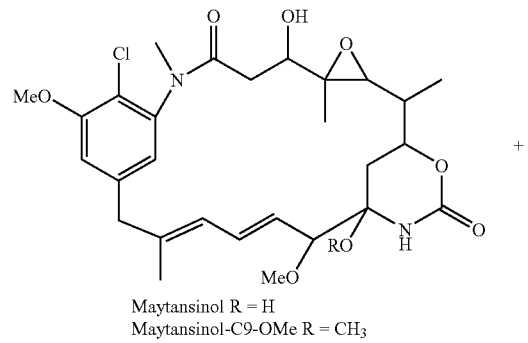

Maytansinol R = H
Maytansinol-C9-OMe R = $CH_3$

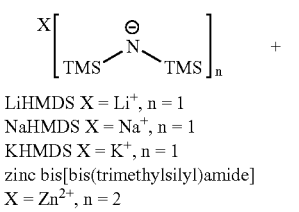

LiHMDS X = $Li^+$, n = 1
NaHMDS X = $Na^+$, n = 1
KHMDS X = $K^+$, n = 1
zinc bis[bis(trimethylsilyl)amide]
X = $Zn^{2+}$, n = 2

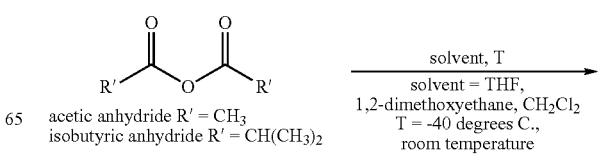

acetic anhydride R' = $CH_3$
isobutyric anhydride R' = $CH(CH_3)_2$ solvent, T
solvent = THF,
1,2-dimethoxyethane, $CH_2Cl_2$
T = -40 degrees C.,
room temperature -continued

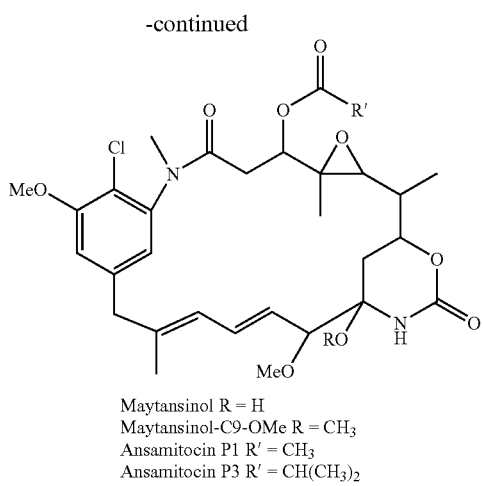

Maytansinol R = H
Maytansinol-C9-OMe R = CH$_3$
Ansamitocin P1 R' = CH$_3$
Ansamitocin P3 R' = CH(CH$_3$)$_2$ Example 1

Maytansinol Esterification with Acetic Anhydride Using Lithium Hexamethyldisilazide (LiHMDS) in Anyhydrous Tetrahydrofuran (THF)

A solution of maytansinol (25.8 mg, 0.046 mmol) in anhydrous THF (1 mL) was prepared in a round bottom flask, equipped with a stir bar and septa and placed under an argon atmosphere. The reaction vessel was cooled to −40° C. in a low form dewar flask containing dry ice and acetone. A solution of 1 M LiHMDS (9.5 mg, 0.057 mmol) in THF was added to the reaction flask dropwise via syringe and the reaction solution was allowed to stir, maintaining the temperature at −40° C. Acetic anhydride (5.6 mg, 0.055 mmol) was added after 15 minutes and the reaction was allowed to proceed, warming slowly over 2 hours. The reaction was quenched by the addition of aqueous ammonium chloride (2 mL) and the crude reaction mixture was transferred to a separatory funnel. The crude product and unreacted starting material were extracted into ethyl acetate twice (2×6 mL), the organic extracts from each extraction were combined, washed with brine (2 mL) and dried over anhydrous Na$_2$SO$_4$. The solvent was evaporated under reduced pressure and the crude residue was purified by preparatory thin layer chromatography (Analtech Uniplate™, 20×20 cm, 1000 micron), eluting in a mixture of methylene chloride and methanol (95:5, v/v). MS: m/z, found: 629.4 (M+Na)$^+$; calculated: 629.2.

Example 2

Maytansinol Esterification with Isobutyric Anhydride Using Lithium Hexamethyldisilazide (LiHMDS) in Anyhydrous 1,2-dimethoxyethane A solution of maytansinol (18.6 mg, 0.033 mmol) was prepared in 1,2-dimethoxyethane (0.8 mL) in a round bottom flask, equipped with a stir bar and placed under an argon atmosphere. The reaction vessel was cooled to −40° C. in a low form dewar flask containing dry ice and acetone. A solution of 1 M LiHMDS (27.6 mg, 0.165 mmol) in anhydrous THF was added to the reaction flask dropwise via syringe and the reaction solution was allowed to stir, maintaining the temperature at −40° C. After 15 minutes, isobutyric anhydride (6.5 mg, 0.041 mmol) was added and the reaction continued to stir for an additional 2.5 hours. Analytical thin layer chromatography (Analtech Uniplate™, 2.5×10 cm, 250 micron), eluting in a mixture of methylene chloride and methanol (95:5, v/v) indicated the formation of the desired C3 isobutyryl ester. The reaction solution was cooled to −40° C., additional isobutyric anhydride (13.1 mg, 0.082 mmol) was added to the reaction flask and the reaction proceeded for an additional 2 hours, warming slowly. Analytical TLC, eluting in a mixture of methylene chloride and methanol (95:5, v/v) indicated the presence of more of the desired product.

Example 3

Maytansinol Esterification with Isobutyric Anhydride Using Sodium Hexamethyldisilazide (NaHMDS) in Anyhydrous Tetrahydrofuran (THF)

A solution of maytansinol (14.mg, 0.026 mmol) in anhydrous THF (0.5 mL) was prepared in a glass vial, equipped with a stir bar and septa and placed under an argon atmosphere. The reaction vessel was cooled to −40° C. in a low form dewar flask containing dry ice and acetone. A solution of 1 M NaHMDS (7.1 mg, 0.039 mmol) in THF was added to the reaction flask dropwise via syringe and the reaction solution was allowed to stir, maintaining the temperature at −40° C. Isobutyric anhydride (6.2 mg, 0.039 mmol) was added after 15 minutes and the reaction was allowed to proceed, warming slowly over 2 hours. Analytical thin layer chromatography (Analtech Uniplate™, 2.5×10 cm, 250 micron), eluting in a mixture of methylene chloride and methanol (95:5, v/v) indicated the formation of the desired C3 isobutyryl ester.

Example 4

Maytansinol Esterification with Isobutyric Anhydride Using Potassium Hexamethyldisilazide (KHMDS) and Crown Ether, 18-crown-6, in Anyhydrous Tetrahydrofuran (THF)

A solution of maytansinol (11.5 mg, 20.3 μmol) in anhydrous THF (0.5 mL) was prepared in a glass vial, equipped with a stir bar and placed under an argon atmosphere. The reaction vessel was cooled to −40° C. in a low form dewar flask containing dry ice and acetone. A solution of KHMDS (6.1 mg, 30.4 μmol) and 18-crown-6 (8.0 mg, 30.4 μmol) in anhydrous THF (0.5 mL) was prepared and added to the reaction flask, maintaining the reaction temperature at −40° C. After 15 minutes, isobutyric anhydride (4.8 mg, 30.4 μmol) was added to the reaction flask; the reaction proceeded, while warming slowly, over 3 hours. Analytical thin layer chromatography (Analtech Uniplate™, 2.5×10 cm, 250 micron), eluting in a mixture of methylene chloride and methanol (95:5, v/v) indicated the formation of the desired C3 isobutyryl ester of maytansinol.

Example 5

Maytansinol Esterification with Isobutyric Anhydride Using Zinc bis[bis(trimethylsilyl)amide] in Anyhydrous Tetrahydrofuran (THF)

A solution of maytansinol (18.7 mg, 0.033 mmol) in anhydrous THF (0.5 mL) was prepared in a glass vial equipped with a stir bar and was maintained under an argon atmosphere. The reaction solution stirred as the zinc bis[bis(trimethylsilyl)amide] (32.1 mg, 0.083 mmol) was added. Isobutyric anhydride (7.8 mg, 0.049 mmol) was added to the reaction vessel after 15 minutes and the reaction proceeded for 2 hours at room temperature. The progress of the reaction was determined by analytical HPLC analysis using an Agilent Zorbax™ C-8 column (4.6×150 mm) at a flow rate of 1.00 mL/min, eluting with a gradient of water and acetonitrile, as follows:

| Time (min) | % A (water) | % B (acetonitrile) |
|---|---|---|
| 0 | 63 | 37 |
| 15 | 58 | 42 |
| 25 | 42 | 58 |
| 35 | 37 | 63 |
| 36 | 63 | 37 |
| 42 | 63 | 37 |

Under these conditions, the desired product eluted with a retention time of 11.11 minutes.

Example 6

Maytansinol-C9-OMe Esterification with Isobutyric Anhydride Using Lithium Hexamethyldisilazide (LiHMDS) in Anyhydrous 1,2-dimethoxyethane A solution of maytansinol-C9-OMe (4.5 mg, 0.008 mmol) in anhydrous 1,2-dimethoxyethane (0.2 mL) was prepared in a glass vial equipped with a stir bar and maintained under an argon atmosphere. The reaction solution was cooled to −40° C. in a low form dewar flask containing dry ice and acetone. A solution of 1 M LiHMDS (6.4 mg, 0.038 mmol) in anhydrous THF was added to the reaction vessel and the solution stirred, maintaining the temperature at −40° C. Isobutyric anhydride (3.0 mg, 0.019 mmol) was added to the reaction vessel after 15 minutes and the reaction was allowed to proceed overnight, while warming slowly. The progress of the reaction was determined by analytical HPLC analysis using an Agilent Zorbax™ C-8 column (4.6×150 mm) at a flow rate of 1.00 mL/min, eluting with a gradient of water and acetonitrile, as follows:

| Time (min) | % A (water) | % B (acetonitrile) |
|---|---|---|
| 0 | 63 | 37 |
| 15 | 58 | 42 |
| 25 | 42 | 58 |
| 35 | 37 | 63 |
| 36 | 63 | 37 |
| 42 | 63 | 37 |

Under these conditions, the desired product eluted with a retention time of 18.33 minutes.

Example 7

Maytansinol-C9-OMe Esterification with Isobutyric Anhydride Using Zinc bis[bis(trimethylsilyl)amide] in Anyhydrous 1,2-dimethoxyethane A solution of maytansinol-C9-OMe (4.4 mg, 7.6 μmol) in anhydrous 1,2-dimethoxyethane (0.2 mL) was prepared in a glass vial equipped with a stir bar and maintained under an argon atmosphere. Zinc bis[bis(trimethylsilyl)amide] (7.3 mg, 18.9 μmol) was added to the reaction vessel and the solution stirred at room temperature. Isobutyric anhydride (3.0 mg, 18.9 μmol) was added to the reaction after 15 minutes and the reaction was allowed to proceed over 4 hours at room temperature. The progress of the reaction was determined by analytical HPLC analysis using an Agilent Zorbax™ C-8 column (4.6×150 mm) at a flow rate of 1.00 mL/min, eluting with a gradient of water and acetonitrile, as follows:

| Time (min) | % A (water) | % B (acetonitrile) |
|---|---|---|
| 0 | 63 | 37 |
| 15 | 58 | 42 |
| 25 | 42 | 58 |
| 35 | 37 | 63 |
| 36 | 63 | 37 |
| 42 | 63 | 37 |

Under these conditions, the desired product eluted with a retention time of 21.2 minutes.

Example 8

Maytansinol Esterification with Isobutyric Anhydride Using Zinc bis[bis(trimethylsilyl)amide] in Anyhydrous Methylene Chloride ($CH_2Cl_2$)

A solution of maytansinol (21.2 mg, 0.037 mmol) in anhydrous $CH_2Cl_2$ (0.5 mL) was prepared in a glass vial equipped with a stir bar and maintained under an argon atmosphere. The reaction solution stirred as the zinc bis[bis(trimethylsilyl)amide] (36.3 mg, 0.094 mmol) was added. Isobutyric anhydride (8.8 mg, 0.055 mmol) was added to the reaction after 15 minutes and the reaction proceeded over 4 hours at room temperature. The progression of the reaction was determined by analytical HPLC analysis using an Agilent Zorbax™ C-8 column (4.6×150 mm) at a flow rate of 1.00 mL/min, eluting with a gradient of water and acetonitrile, as follows:

| Time (min) | % A (water) | % B (acetonitrile) |
|---|---|---|
| 0 | 63 | 37 |
| 15 | 58 | 42 |
| 25 | 42 | 58 |
| 35 | 37 | 63 |
| 36 | 63 | 37 |
| 42 | 63 | 37 |

Under these conditions, the desired product eluted with a retention time of 10.99 min.

Example 9

Maytansinol Esterification with Isobutyric Anhydride Using Zinc bis[bis(trimethylsilyl)amide] in Anyhydrous 1,2-dimethoxyethane A solution of maytansinol (15.8 mg, 0.028 mmol) in anhydrous 1,2-dimethoxyethane (0.5 mL) was prepared in a glass vial equipped with a stir bar and was maintained under an argon atmosphere. The reaction solution stirred as zinc bis[bis(trimethylsilyl)amide] (27.0 mg, 0.070 mmol) was added. Isobutyric anhydride (6.7 mg, 0.042 mmol) was added to the reaction after 15 minutes and the reaction proceeded over 2 hours at room temperature. The progression of the reaction was determined by analytical HPLC analysis using an Agilent Zorbax C-8 column (4.6×150 mm) at a flow rate of 1.00 mL/min, eluting with a gradient of water and acetonitrile, as follows:

| Time (min) | % A (water) | % B (acetonitrile) |
| --- | --- | --- |
| 0 | 63 | 37 |
| 15 | 58 | 42 |
| 25 | 42 | 58 |
| 35 | 37 | 63 |
| 36 | 63 | 37 |
| 42 | 63 | 37 |

Under these conditions, the desired product eluted with a retention time of 10.65 minutes.

Example 10

Maytansinol Esterification with Isobutyric Anhydride Using Zinc bis[bis(trimethylsilyl)amide] and Crown Ether, 18-crown-6, in Anyhydrous Methylene Chloride ($CH_2Cl_2$)

A solution of maytansinol (14.6 mg, 0.026 mmol) in anhydrous $CH_2Cl_2$ (0.3 mL) was prepared in a glass vial equipped with a stir bar and was maintained under an argon atmosphere. The reaction solution stirred as zinc bis[bis(trimethylsilyl)amide] (25.1 mg, 0.065 mmol) was added followed by the addition of a solution of 18-crown-6 (17.2 mg, 0.065 mmol) in $CH_2Cl_2$ (0.2 mL). Isobutyric anhydride (6.7 mg, 0.042 mmol) was added to the reaction after 15 minutes and the reaction proceeded over 2 hours at room temperature. The progression of the reaction was determined by analytical HPLC analysis using an Agilent Zorbax™ C-8 column (4.6×150 mm) at a flow rate of 1.00 mL/min, eluting with a gradient of water and acetonitrile, as follows:

| Time (min) | % A (water) | % B (acetonitrile) |
| --- | --- | --- |
| 0 | 63 | 37 |
| 15 | 58 | 42 |
| 25 | 42 | 58 |
| 35 | 37 | 63 |
| 36 | 63 | 37 |
| 42 | 63 | 37 |

Under these conditions, the desired product eluted with a retention time of 11.88 minutes.

Example 11

Maytansinol Esterification with N-methyl-N-(4-methyldithio-4-methyl-1-oxopropyl)-L-alanine Using Zinc bis[bis(trimethylsilyl)amide] in Anyhydrous Methylene Chloride ($CH_2Cl_2$)

Reaction Scheme

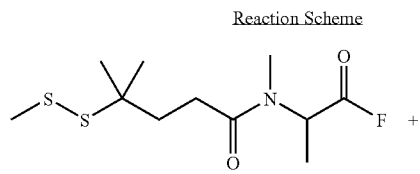

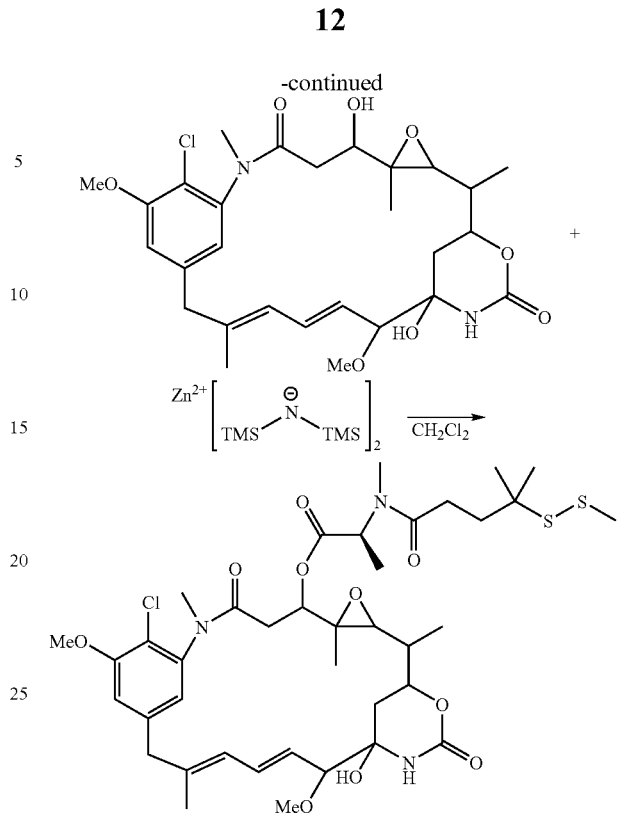

A solution of N-(4-methyldithio-4-methyl-1-oxopropyl)-L-alanine (87.3 mg, 0.313 mmol) in $CH_2Cl_2$ (0.5 mL) was prepared in a glass vial, equipped with a stir bar and cooled to 0° C. in an ice bath. N,N-diisopropylethylamine (60.6 mg, 0.469 mmol) and [bis(2-methoxyethyl)amino] sulfur triflouride (83.1 mg, 0.375 mmol) were sequentially added to the reaction vial. The reactants continued to stir for 30 minutes at a maintained temperature of 0° C., A solution of maytansinol (29.5 mg, 0.052 mmol) and zinc bis[bis(trimethylsilyl)amide] (240.9 mg, 0.624 mmol) in $CH_2Cl_2$ (0.5 mL) was added to the reaction vessel after acyl fluoride formation. The reaction proceeded at 0° C. for 15 minutes after which time the ice bath was removed and the reaction continued overnight at room temperature under an argon atmosphere. Analytical thin layer chromatography (Analtech Uniplate™, 2.5×10 cm, 250 micron), eluting in a mixture of methylene chloride and methanol (95:5, v/v) indicated the formation of the desired N-methyl-L-alanyl ester of maytansinol at C3. The degree of conversion of the reaction was determined by analytical HPLC analysis using a Vydac™ protein & peptide C18 column (4.6×250 mm) at a flow rate of 1.50 mL/min, eluting with a gradient of water and acetonitrile, as follows:

| Time (min) | % A (water) | % B (acetonitrile) |
| --- | --- | --- |
| 0 | 95 | 5 |
| 2.5 | 95 | 5 |
| 32 | 5 | 95 |
| 35 | 5 | 95 |

Under these conditions, the desired product eluted with a retention time of 23.07 min with no detected D-isomer. MS: m/z found 848.8 ($M+Na^+$) calculated 849.4.

Example 12

Maytansinol Esterification with N-methyl-N-(4-methyldithio-4-methyl-1-oxopropyl)-L-alanine using Zinc bis[bis(trimethylsilyl)amide] in Anyhydrous Methylene Chloride (CH$_2$Cl$_2$)

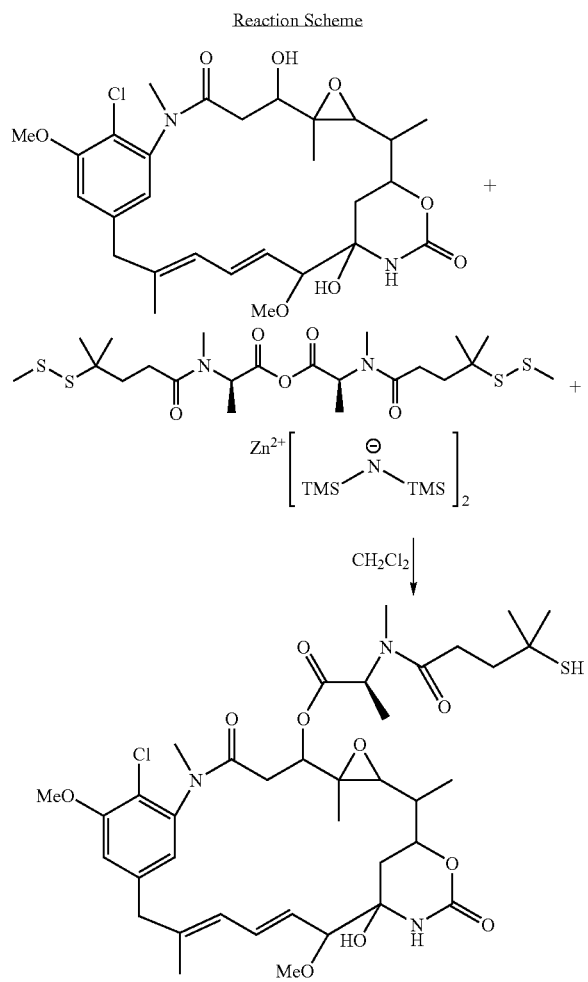

A solution of N-methyl-N-(4-methyldithio-4-methyl-1-oxopropyl)-L-alanine (36.6 mg, 0.313 mmol) and 1,3-dicyclohexylcarbodiimide (13.51 mg, 0.065 mmol) was prepared in CH$_2$Cl$_2$ (0.5 mL) in a round bottom flask equipped with a stir bar and maintained under an argon atmosphere. The solution stirred vigorously at room temperature for 30 minutes as the symmetrical anhydride formed. The reaction mixture was filtered through glass wool and added to a reaction flask containing maytansinol (12.3 mg, 0.022 mmol) and zinc bis[bis(trimethylsilyl)amide] (42.5 mg, 0.109 mmol) prepared in CH$_2$Cl$_2$ (1 mL). The reaction proceeded at room temperature under an argon atmosphere with stirring. After 3 hours, an additional 5 equivalents of zinc bis[bis(trimethylsilyl)amide] (42.5 mg, 0.109 mmol) were added to the reaction vessel and the reaction proceeded overnight. Analytical thin layer chromatography (Analtech Uniplate™, 2.5×10 cm, 250 micron), eluting in a mixture of methylene chloride and methanol (95:5, v/v) indicated the formation of the desired N-methyl-L-alanyl ester of maytansinol at C3. The degree of conversion of the reaction was determined by analytical HPLC analysis using a Vydac™ protein & peptide C18 column (4.6×250 mm) at a flow rate of 1.50 mL/min, eluting with a gradient of water and acetonitrile, as follows:

| Time (min) | % A (water) | % B (acetonitrile) |
| --- | --- | --- |
| 0 | 95 | 5 |
| 2.5 | 95 | 5 |
| 32 | 5 | 95 |
| 35 | 5 | 95 |

Under these conditions the thiol containing product eluted at 20.75 min with no detected D-isomer. MS: m/z found 780.8 (M+Na$^+$) calculated 781.4.

Example 13

Synthesis of Ic

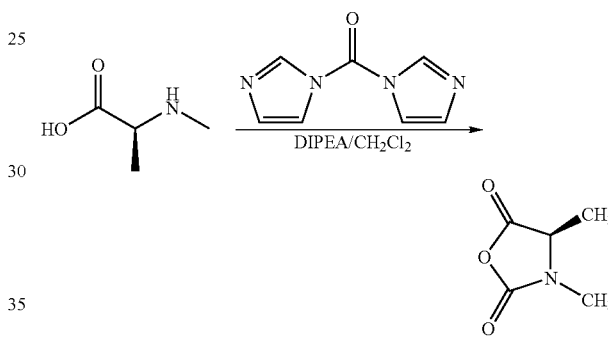

To 50.2 mg of N-methyl-L-alanine suspended in 60 ml of CH$_2$Cl$_2$ was added 0.186 ml of DIPEA. After the solid mass had been broken up into a fine suspension by sonication, 82.6 mg of 1,1'-carbonyldiimidazole was added in 5 portions over 4 hours. The reaction was stirred over night, then filtered through a short silica column with dichloromethane. The filtrate was evaporated and crystallized with ether/hexane to afford 28 mg (45% Yield) of product. $^1$H NMR (DMSO) 4.40 (1H, dd, J=7.0, 14.1 Hz, CH), 2.84 (3H, s, N-CH3), 1.38 (3H, d, J=7.1 Hz); $^{13}$C NMR 194.83, 184.18, 56.70, 27.97, 14.09; MS M-168.8 (M+K-1), 153.8 (M+Na-1).

Compound Id can be prepared in a similar manor from N-methyl-D-alanine. Compound Ic can also be prepared by the reaction of phosgene on N-methyl-L-alanine.

Reaction Figure

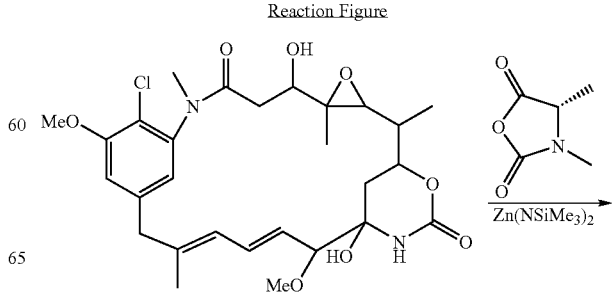

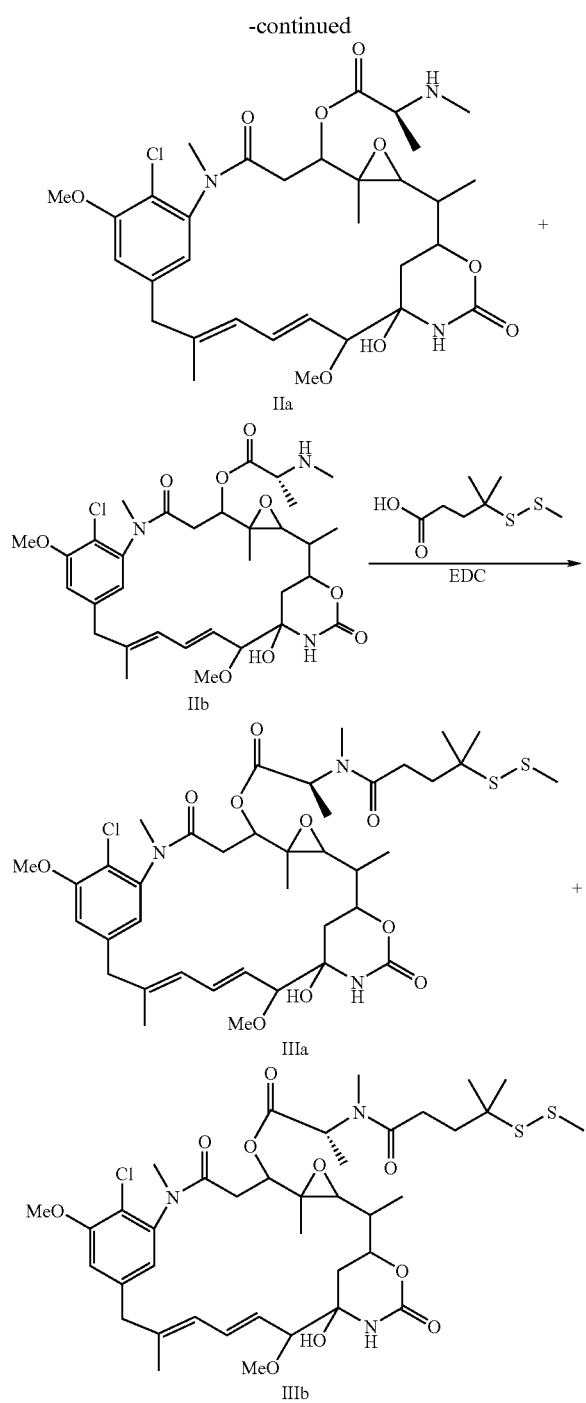

Example 14

Maytansinol Esterification with Ic Using Zinc bis[bis(trimethylsilyl)amide] in Anhydrous Dimethyl Formamide (DMF) Followed by Amide Formation with 4-methyldithio-4-methyl-pentanoic Acid (MMP).

Maytansinol (20 mg, 0.035 mmol) and Ic (27 mg, 0.21 mmol) were dissolved in 0.30 mL of dimethylformamide. The solution was vigorously stirred under an argon atmosphere as zinc bis[bis(trimethylsilyl)amide] (81 mg, 0.21 mmol) was added dropwise. The reaction was stirred for 3 hours then analyzed using HPLC method 2, described below, with dual detection (254 nm absorbance and mass spectroscopy). Analysis showed a 50% conversion to desired IIa, retention time 10 min, 5% conversion to undesired IIb retention time 12.8 min, and 25% unreacted maytansinol retention time 12.8 min. The IIa and IIb products are unstable so they were not isolated, the reaction mixture was extracted with 0.20 mL of 1:1 saturated NaHCO$_3$: saturated NaCl and 1 mL of ethyl acetate. To the organic layer was added 4-methyldithio-4-methyl-pentanoic acid (68 mg, 0.35 mmol) and 1-[3-(dimethylamino)propyl]-3-ethylcarbodiimide hydrochloride (EDC-HCl 66 mg, 0.35 mmol). The mixture was stirred for 2 hours. Analysis using HPLC method 2 showed that all of the IIa and IIb had reacted to give a 95:5 mixture of IIIa:IIIb. The solution was washed with 0.3 mL of 0.25% aqueous HCl followed by a wash with 0.2 mL saturated NaCl. Solvent was removed by evaporation under vacuum and the residue was purified by silica chromatography using CH$_2$Cl$_2$:MeOH 94:6 as the mobile phase followed by purification using a 250×10 mm 5 micron partical size Kromasil™ CN bonded silica column with an isocratic mobile phase of hexanes:ethyl acetate:2-propanol 68:8:24, IIIa retention time 10 min, IIIb retention time 19 min. Solvent was evaporated under vacuum to give 11.6 mg of desired IIIb (0.014 mmol, 40% overall yield from maytansinol). MS: m/z found 848.9 (M+Na) calculated (849.4).

HPLC method 2:

Column: C8 Kromasil™ 150×2.0 mm 5 micron particle size.

Fow rate: 0.22 mL/min.

Temperature: Ambient.

Sample preparation: 10 microliters of reaction mixture was added to 500 microliters of 10:1 acetonitrile:acetic acid.

Injection volume: 4 microliters.

Mobile phase: A=deionized water containing 0.1% trifluoroacetic acid; B=acetonitrile Gradient

| Time | % A | % B |
| --- | --- | --- |
| 0 | 75 | 25 |
| 9 | 58 | 42 |
| 15 | 42 | 58 |
| 18 | 20 | 80 |
| 19 | 75 | 25 |
| 24 | 75 | 25 |

All publications and other references cited herein are expressly incorporated by reference in their entireties.

We claim:

1. A process of making a maytansinoid ester comprising forming an anion of maytansinol or a maytansinoid bearing a free C-3 hydroxyl moiety and reacting the anion with an activated carboxyl compound to thereby produce the maytansinoid ester.

2. The process of claim 1, wherein the anion is formed by reacting the maytansinol or the maytansinoid bearing a free C-3 hydroxyl moiety with a non-aqueous base.

3. The process of claim 2, wherein the non-aqueous base is a metal hexamethyldisilazide, an alkyl metal, an aryl metal, a metal hydride, sodamide, or potassium amide.

4. The process of claim 3, wherein the metal hexamethyldisilazide is zinc hexamethyldisilazide, sodium hexamethyldisilazide, lithium hexamethyldisilazide, or potassium hexamethyldisilazide.

5. The process of claim 3, wherein the alkyl metal or aryl metal is methyl lithium, n-butyl lithium, tert-butyl lithium, phenyl lithium, lithium di-isopropylamide (LDA), pentyl sodium, or 2-phenyl isopropyl-potassium.

6. The process of claim 3, wherein the metal hydride is sodium hydride or potassium hydride.

7. The process of claim 1, wherein the activated carboxyl compound is at least one member selected from the group consisting of an acid anhydride, a mixed anhydride, a cyclic anhydride, an acid halide, an acylimidizolide, an acyl substituted imidazolide, and a carboxyl ester.

8. The process of claim 7, wherein the acid anhydride is selected from acetic anhydride, isobutyric anhydride, or an anhydride of an amino acid derivative.

9. The process of claim 7, wherein the mixed anhydride is selected from the group consisting of a mixed anhydride between a phosphate or sulfate with the acid moiety of acetic acid, propionic acid, butyric acid or an amino acid derivative.

10. The process of claim 7, wherein the cyclic anhydride is selected from the group consisting of an N-carboxyanhydride of N-methyl-L-alanine and an N-carboxyanhydride of N-methyl-D-alanine.

11. The process of claim 7, wherein the acid halide is an acid fluoride, an acid chloride, an acid bromide or an acid iodide.

12. The process of claim 7, wherein the carboxyl ester is a N-hydroxysuccinimide ester, a para-nitrophenyl ester, an ortho-nitrophenyl ester, a dinitrophenyl ester, or a pentafluorophenyl ester.

13. The process of claim 1, wherein the activated carboxyl compound is a compound of formula RCOX, wherein X is a halide, an alkoxy group, an aryloxy group, an imidazole or —OY, wherein Y is succinimide, phthalimide, aryl or substituted aryl, and R is a linear, branched or cyclic alkyl or alkenyl having from 1 to 10 carbon atoms or a substituted amino acid moiety.

14. The process of claim 13, wherein the substituted amino acid moiety is N-methyl-L-alanyl moiety.

15. The process of claim 13, wherein X is fluoride, chloride, bromide or iodide, pyridyl, imidazolyl or substituted imidazolyl, or —OY, wherein Y is succinimide, phthalimide, aryl or substituted aryl.

16. The process of claim 13, wherein the substituted aryl is at least one member selected from the group consisting of para-nitrophenyl, ortho-nitrophenyl, dinitrophenyl and pentafluorophenyl.

17. The process of claim 1, wherein the activated carboxyl compound is an acid anhydride of the formula RCOOCOR', wherein R and R' are the same or different and are a linear, branched or cyclic alkyl or alkenyl having from 1 to 10 carbon atoms or a substituted amino acid moiety.

18. The process of claim 17, wherein the substituted amino acid moiety is N-methyl-L-alanyl moiety.

19. The process of claim 1, wherein the activated carboxyl compound is a carboxyl-activated amino acid containing compound.

20. The process of claim 19, wherein the carboxyl-activated amino acid containing compound is a compound of the formula (Ia), (Ib), (Ic) or (Id):

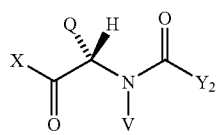
(Ia)

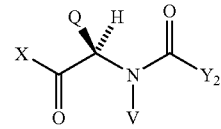
(Ib)

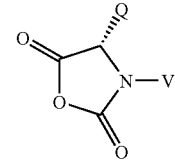
(Ic)

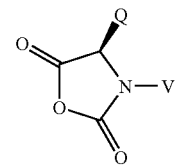
(Id)

wherein:

X represents a halide, an alkoxy group, an aryloxy group, an imidazole, —OY, wherein Y is succinimide, phthalimide, aryl or substituted aryl, an anhydride or a mixed anhydride; Q represents H, or a branched or linear alkyl group; V represents H, or a branched or linear alkyl group; and $Y_2$ represents $(CR_7R_8)_l(CR_5R_6)_m(CR_3R_4)_n CR_1R_2(SZ_2)_p$, wherein: $R_1$ and $R_2$ are each independently H, linear, branched or cyclic alkyl or alkenyl having from 1 to 10 carbon atoms, phenyl or substituted phenyl, and in addition $R_2$ can be H; $R_3$, $R_4$, $R_5$, $R_6$, $R_7$ and $R_8$ are each independently H, linear, branched or cyclic alkyl or alkenyl having from 1 to 10 carbon atoms, phenyl or substituted phenyl; l, m and n are each independently 0 or an integer of from 1 to 5; $Z_2$ is $R_9$, $SR_9$ or $COR_9$, wherein $R_9$ is linear alkyl, branched alkyl or cyclic alkyl having from 1 to 10 carbon atoms, or simple or substituted aryl or heterocyclic, p is either 0 or 1.

21. The process of claim 20, wherein X is fluoride, chloride, bromide, iodide, pyridyl, imidazolyl, substituted imidazolyl, or —OY, wherein Y is succinimide, phthalimide, aryl or substituted aryl.

22. The process of claim 20, wherein X is —OCOR$_9$, wherein R$_9$ is linear alkyl, branched alkyl or cyclic alkyl having from 1 to 10 carbon atoms, or simple or substituted aryl or heterocyclic.

23. The process of claim 20, wherein X is a substituent that gives a symmetrical anhydride of formula (Ia) or (Ib).

24. The process of claim 1, 12 or 20, wherein the anion is formed by reacting the maytansinol or a maytansinoid bearing a free C-3 hydroxyl moiety with zinc hexamethyldisilazide.

25. The process of claim 1, 12 or 20, wherein the activated carboxyl group is an acid fluoride.

26. The process of claim 1, 12 or 20, wherein the maytansinoid ester is substantially a single diastereomer.

27. The process of claim 26, wherein the diastereomer is an L-aminoacyl ester.

* * * * *